United States Patent
Udayakumar

(10) Patent No.: US 12,251,331 B2
(45) Date of Patent: Mar. 18, 2025

(54) SKIN BARRIER INCLUDING SKIN FRIENDLY INGREDIENTS

(71) Applicant: Hollister Incorporated, Libertyville, IL (US)

(72) Inventor: Bettakeri S. Udayakumar, Darien, IL (US)

(73) Assignee: Hollister Incorporated, Libertyville, IL (US)

( * ) Notice: Subject to any disclaimer, the term of this patent is extended or adjusted under 35 U.S.C. 154(b) by 420 days.

(21) Appl. No.: 16/613,350

(22) PCT Filed: May 24, 2018

(86) PCT No.: PCT/US2018/034321
§ 371 (c)(1),
(2) Date: Nov. 13, 2019

(87) PCT Pub. No.: WO2018/226417
PCT Pub. Date: Dec. 13, 2018

(65) Prior Publication Data
US 2020/0188160 A1    Jun. 18, 2020

Related U.S. Application Data

(60) Provisional application No. 62/516,892, filed on Jun. 8, 2017.

(51) Int. Cl.
*A61F 5/443*     (2006.01)

(52) U.S. Cl.
CPC .................................. *A61F 5/443* (2013.01)

(58) Field of Classification Search
CPC .......... A61F 5/443; A61F 4/445; A61F 5/448; A61F 5/4408; A61F 5/4404
See application file for complete search history.

(56) References Cited

U.S. PATENT DOCUMENTS

| | | | |
|---|---|---|---|
| 3,373,745 A | | 3/1968 | Benfield et al. |
| 3,908,658 A | * | 9/1975 | Marsan ................ A61L 24/043 604/336 |
| 5,158,555 A | | 10/1992 | Porzilli |
| 5,336,209 A | | 8/1994 | Porzilli |
| 5,492,943 A | | 2/1996 | Stempel |
| 5,496,296 A | | 3/1996 | Holmberg |

(Continued)

FOREIGN PATENT DOCUMENTS

| | | |
|---|---|---|
| EP | 1053725 A1 | 11/2000 |
| EP | 2159255 A1 | 3/2010 |

(Continued)

OTHER PUBLICATIONS

Written Opinion issued by ISA/EPO in connection with PCT/US2018/034321 on Aug. 2, 2018.

(Continued)

*Primary Examiner* — Rebecca E Eisenberg
*Assistant Examiner* — Rachel O'Connell
(74) *Attorney, Agent, or Firm* — Klintworth & Rozenblat IP LLP

(57) ABSTRACT

A skin barrier for an ostomy appliance includes at least one layer of skin barrier material and skin friendly ingredients provided only on a skin contact surface or in a skin contact layer of the skin barrier.

6 Claims, 3 Drawing Sheets

(56) References Cited

U.S. PATENT DOCUMENTS

| | | |
|---|---|---|
| 5,811,116 A | 9/1998 | Gilman et al. |
| 6,186,989 B1 | 2/2001 | Horie |
| 6,333,041 B1 | 12/2001 | Hoath et al. |
| 6,589,222 B1 | 7/2003 | Olsen |
| 6,764,474 B2 | 7/2004 | Nielsen et al. |
| 7,576,256 B2 | 8/2009 | Bjoernberg et al. |
| 7,951,127 B2 | 5/2011 | Sanabria et al. |
| 8,237,009 B2 | 8/2012 | Siniaguine |
| 8,247,634 B2 | 8/2012 | Siniaguine |
| 8,439,884 B2 | 5/2013 | Fabo et al. |
| 8,545,468 B2 | 10/2013 | Fabo et al. |
| 8,652,112 B2 | 2/2014 | Johannison et al. |
| 8,673,992 B2 | 3/2014 | Eckstein |
| 8,979,813 B2 | 3/2015 | Uveborn |
| 9,039,668 B2 | 5/2015 | Svensby et al. |
| 9,084,696 B2 | 7/2015 | Luce |
| 9,233,019 B2 | 1/2016 | Lykke et al. |
| 9,241,835 B2 | 1/2016 | Zepeda |
| 9,271,863 B2 | 3/2016 | Stroebech et al. |
| 9,452,079 B2 | 9/2016 | Lykke et al. |
| 9,474,827 B2 | 10/2016 | Blucher et al. |
| 2003/0225387 A1 | 12/2003 | Zedlitz |
| 2005/0010180 A1* | 1/2005 | Wang ................ A61F 5/443 977/841 |
| 2005/0096611 A1* | 5/2005 | Stoyer ................ A61F 5/443 604/332 |
| 2005/0143696 A1* | 6/2005 | Pedersen ................ A61F 5/441 604/332 |
| 2005/0163978 A1 | 7/2005 | Strobech et al. |
| 2006/0018955 A1 | 1/2006 | Debusk et al. |
| 2006/0228318 A1 | 10/2006 | Fabo |
| 2008/0103207 A1 | 5/2008 | Dayan |
| 2009/0216168 A1 | 8/2009 | Eckstein |
| 2009/0312685 A1* | 12/2009 | Olsen ................ A61F 5/443 604/386 |
| 2010/0191201 A1* | 7/2010 | Bach ................ A61L 24/043 604/336 |
| 2011/0245789 A1 | 10/2011 | Buus |
| 2012/0209229 A1 | 8/2012 | Nordby et al. |
| 2013/0261576 A1 | 10/2013 | Stroebech et al. |
| 2013/0281904 A1 | 10/2013 | Jackson et al. |
| 2014/0276324 A1 | 9/2014 | Zepeda et al. |
| 2014/0303541 A1 | 10/2014 | Vachon |
| 2015/0024018 A1 | 1/2015 | Faucher et al. |
| 2015/0094672 A1 | 4/2015 | Blucher et al. |
| 2015/0157758 A1 | 6/2015 | Blucher et al. |
| 2015/0223966 A1* | 8/2015 | Mahood ................ A61F 5/4407 604/337 |
| 2015/0238651 A1* | 8/2015 | Dong ................ A61L 24/0005 524/313 |
| 2015/0250639 A1 | 9/2015 | Thirstrup et al. |
| 2015/0257923 A1 | 9/2015 | Thirstrup et al. |
| 2015/0282997 A1 | 10/2015 | Aritzi et al. |
| 2015/0282998 A1 | 10/2015 | Aritzi et al. |
| 2015/0297389 A1 | 10/2015 | Nyberg |
| 2015/0320585 A1 | 11/2015 | Fattman et al. |
| 2015/0351952 A1* | 12/2015 | Hewitt ................ B29C 65/02 604/336 |
| 2015/0359656 A1 | 12/2015 | Hansen et al. |
| 2016/0030249 A1 | 2/2016 | Canepelle et al. |
| 2016/0030250 A1 | 2/2016 | Canepelle et al. |
| 2016/0143768 A1 | 5/2016 | Stroebech et al. |
| 2016/0151197 A1* | 6/2016 | Johnsen ................ A61F 5/448 604/336 |
| 2016/0317356 A1 | 11/2016 | Corley |
| 2016/0324816 A1 | 11/2016 | Swanick et al. |
| 2016/0338969 A1 | 11/2016 | Greenhalgh et al. |
| 2017/0112658 A1* | 4/2017 | Hosono ................ A61F 5/445 |

FOREIGN PATENT DOCUMENTS

| | | |
|---|---|---|
| EP | 2165718 A1 | 3/2010 |
| GB | 2423267 A | 8/2006 |
| GB | 2428381 A | 1/2007 |
| JP | H02502884 A | 9/1990 |
| JP | 2007515256 A | 6/2007 |
| JP | 2011516219 A | 5/2011 |
| JP | 2014198175 A | 10/2014 |
| WO | 94/15562 A1 | 7/1994 |
| WO | 2010037882 A1 | 4/2010 |
| WO | 2016076514 A1 | 5/2016 |
| WO | 2016146135 A1 | 9/2016 |

OTHER PUBLICATIONS

International Search Report issued by ISA/EPO in connection with PCT/US2018/034321 on Aug. 2, 2018.

International Report on Patentability issued by WIPO in connection with PCT/US2018/034321 dated Dec. 19, 2019.

\* cited by examiner

SKIN BARRIER INCLUDING SKIN FRIENDLY INGREDIENTS

This is a National Stage Application of International Patent Application No. PCT/US2018/034321, filed May 24, 2018, which claims the benefit of and priority to U.S. Provisional Application No. 62/516,892, filed Jun. 8, 2017, the entirety of which are incorporated fully herein by reference.

BACKGROUND

The present disclosure relates to skin-adhering devices, and more particularly to skin barriers for securing ostomy appliances to skin surfaces of users.

An ostomy appliance is a medical device or prosthetic that provides a means for collecting waste from a stoma typically created as a result of a surgical procedure to divert a portion of the colon or small intestine. One type of ostomy appliance is a pouch that is attached to a user around the stoma or the peristomal area.

Typically, an ostomy wafer including a skin barrier, a backing layer and an inlet opening for receiving a stoma is used to secure an ostomy pouch to a user. The ostomy wafer may be attached to an ostomy pouch for a one-piece pouch system. Alternatively, the ostomy wafer may be configured as a faceplate for a two-piece pouch system including a body-side coupling that is configured to engage a pouch-side coupling attached to an ostomy pouch.

The skin barriers may remain adhered to a user's skin for extended periods to secure an ostomy pouch. Thus, the skin barriers should have sufficient adhesive strength, yet not be so aggressive as to risk skin injury or irritation during use and upon removal. Due to the extensive wear time, it is desirable that skin barriers include ingredients to minimize skin irritation and promote skin health.

A skin barrier including ceramide has been developed and available through the Applicant of the present application under the trade name, CeraPlus®. However, adding skin health ingredients, such as ceramide, into skin barriers can become costly, and may be limited due to possible interactions between skin healthy ingredients and skin barrier materials. Further, a large portion of skin friendly ingredients dispersed in the skin barrier matrix may not migrate to the skin contact surface. Thus, the present disclosure provides an improved skin barrier including skin friendly ingredients.

BRIEF SUMMARY

In one aspect, an ostomy appliance comprising at least one skin friendly ingredient is provided. The ostomy appliance may be formed from at least one skin barrier material or at least one stoma base sealing material. The at least one skin friendly ingredient may be provided only on a skin contact surface or only in a skin contact layer of the ostomy appliance.

In an embodiment, the ostomy appliance may be an ostomy wafer comprising a baking layer, a skin barrier, and an inlet opening for receiving a stoma. The skin barrier may be formed from at least one skin barrier material, and the backing layer may be laminated to a distal surface of the skin barrier. The at least one skin barrier material may be a hydrocolloid adhesive.

The at least one skin friendly ingredient may be provided only on a skin contact surface of the skin barrier. In some embodiments, the skin barrier may include a skin contact layer and an inner layer, wherein the at least one skin friendly ingredient may be dispersed in the skin contact layer. In such embodiments, a thickness of the skin contact layer may be less than a thickness of the inner layer.

In an embodiment, the ostomy wafer may be attached to a pouch for a one-piece ostomy pouch system. In another embodiment, the ostomy wafer may further include a body-side coupling ring configured to engage a pouch-side coupling ring attached to a pouch in a two-piece ostomy pouch system.

In another embodiment, the ostomy appliance may be a stoma ring formed from at least one stoma sealing material. The at least one stoma sealing material may comprise a hydrocolloid adhesive and/or a silicone adhesive. The at least one skin friendly ingredient may be provided only on outer surfaces of the stoma ring.

In an embodiment, the stoma ring may include a first outer layer, a second outer layer, and an inner layer therebetween, wherein the at least one skin friendly ingredient may be dispersed in the first and second outer layers.

In any of the foregoing embodiments, at least one skin friendly ingredient may be provided in a pattern. For example, the at least one skin friendly ingredient may be provided in a pattern of concentric circles. In an embodiment, the at least one skin friendly ingredient may be provided on the skin contact surface in a pattern having a thickness, wherein the at least one skin friendly ingredient may be injected into the at least one skin barrier material or at least one stoma sealing material proximate the skin contact surface.

In yet another aspect, a method of making an ostomy appliance is provided. The method may include the steps of forming the ostomy appliance from at least one skin barrier material or at least one stoma sealing material, and providing at least one skin friendly ingredient only on a skin contact surface or only in a skin contact layer.

In an embodiment, the step of providing at least one skin friendly ingredient may include providing the at least one skin friendly ingredient in a powder form and sprinkled the same on the skin contact surface of the ostomy appliance. In another embodiment, the step of providing at least one skin friendly ingredient may include dissolving the at least one skin friendly ingredient in a solvent or water and spraying the same on the skin contact surface of the ostomy appliance. In yet another embodiment, the step of providing at least one skin friendly ingredient may include injecting the least one skin friendly ingredient into the ostomy appliance proximate to the skin contact surface using a device comprising micro-needles.

In yet another embodiment, the ostomy appliance may be formed by pressing the at least one skin barrier material or at least one stoma sealing material on a release liner. In such an embodiment, the method may include a step of applying the at least one skin friendly ingredient on the release liner prior to the pressing step, such that when the skin barrier material is pressed and the release liner is removed, the at least one skin friendly ingredient transfers to the skin contact surface of the at least one skin barrier material or the at least one stoma sealing material. The pressing step may be performed during manufacturing of ostomy appliances. In another embodiment, a user may be instructed to carry out the pressing step before removing the release liner.

In an embodiment, the ostomy appliance may include a skin contact layer formed from a skin barrier material or a stoma sealing material and an inner layer formed from a skin barrier material or a stoma sealing material. The skin contact layer and the inner layer may be coextruded, wherein a skin barrier formulation or a stoma sealing formulation for the skin contact layer may contain the at least one skin friendly ingredient to form the skin contact layer comprising the at least one skin friendly ingredient dispersed therein.

In any of the foregoing embodiments, the at least one skin friendly ingredient may be selected from various materials that protect skin, reduce skin irritation, aid healing, and/or promote skin health, such as vitamin E, ceramide, cholesterol, fatty acids, micro-pockets of pH buffers, polysaccharides, and anti-wrinkle agents.

The method of providing at least one skin friendly ingredient only on a skin contact surface or only in a skin contact layer according to the foregoing embodiments may be used to make other skin contact products, such as wound care products.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
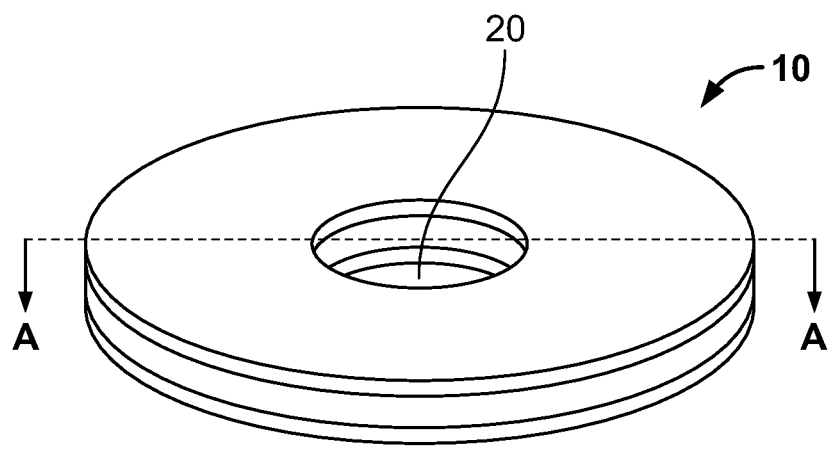
FIG. 1 is a perspective view of an ostomy wafer including a skin barrier according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated.

Figure 2:
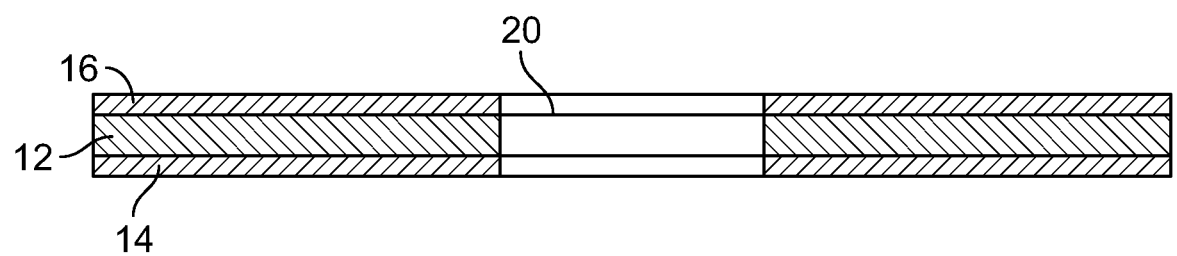
FIG. 2 is a cross-sectional view of the ostomy wafer of FIG. 1 taken along line A-A.
Figure 3:
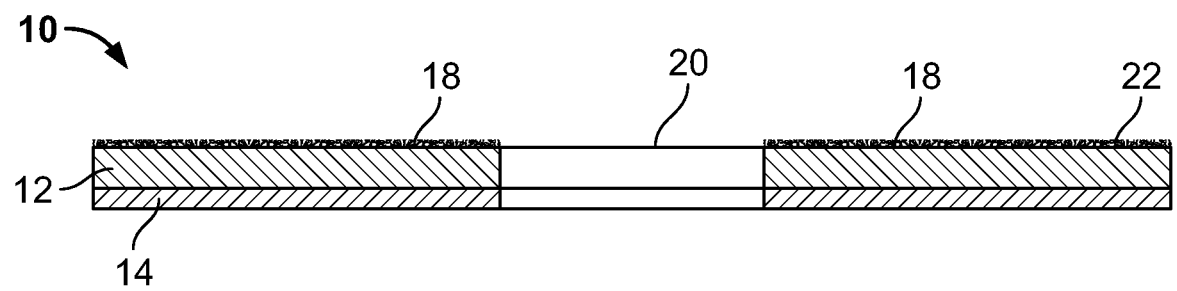
FIG. 3 is a cross-sectional view of the ostomy wafer of FIG. 1 with a release liner removed from the ostomy wafer.

Referring to FIGS. 1-3, an embodiment of an ostomy wafer 10 for an ostomy appliance is shown. The ostomy wafer 10 may generally include a skin barrier 12, a backing layer 14, a release liner 16, and inlet opening 20 for receiving a stoma. As best shown in FIG. 3, the skin barrier 12 may include skin friendly ingredients 18 provided only on a skin contact surface 22 of the skin barrier 12.

The skin friendly ingredients may include materials that protect skin, reduce skin irritation, aid healing, and/or promote skin health, such as collagen boosters. Suitable skin friendly ingredients include, but are not limited to, vitamin E, vitamin A, vitamin C, aloe vera extract, ceramide, cholesterol, fatty acids, polysaccarides, such as Karaya, anti-wrinkle agents, anti-inflammatory/soothing agents, such as ginkgolide A, hydrolyzed collagen, alpha-amyrin, beta-amyrin, oleanolic acid, and antiperspirants, such as Alcloxa. In an embodiment, the skin friendly ingredients 18 may comprise fatty acids, which may function as antimicrobial agent, anti-viral agent, anti-inflammatory agent, and/or anti-fungal agent that can combat fungal infections prevalent in ostomates. For example, the skin friendly ingredients 18 may comprise fatty acids from coconut oil having antibacterial, antifungal and anti-inflammatory properties. In another embodiment, the skin friendly ingredients 18 may comprise anti-wrinkle agents to minimize skin crevices proximate a stoma base to provide a smooth surface to improve barrier adhesion. For example, the skin friendly ingredients may comprise rose oil having anti-wrinkle, antimicrobial, and anti-inflammatory properties. Yet in another embodiment, the skin friendly ingredients 18 may comprise micro-encapsulated pain relieving ingredients configured to release when exposed to stoma effluent. The skin friendly ingredients 18 may also comprise micro-pockets of pH buffers.

The skin friendly ingredients may be provided in various forms, for example, fine powder, liquid, or encapsulated, such as encapsulated skin health formulations available from Salvona, Hamilton, N.J. Some skin friendly ingredients may be dissolved in a solvent or water.

The skin barrier 12 may be formed from a suitable medical grade adhesive, such as various hydrocolloid adhesives comprising water absorbing hydrocolloid particles dispersed in skin friendly adhesive compositions. In an embodiment, the skin barrier 12 may be formed from an adhesive composition comprising viscoelastic adhesive elastomers, such as polyisobutylene and styrene block copolymer, tackifier, antioxidant, and hydrocolloids, such as sodium carboxymethylcellulose. An example of such hydrocolloid adhesive compositions is disclosed in U.S. Pat. No. 5,492,943, which is assigned to Applicant of the present application and incorporated fully by reference herein. Other suitable skin barrier materials may include, but are not limited to, silicone based adhesives and acrylic adhesives.

In an embodiment, at least one skin friendly ingredient, such as particles of vitamin E encapsulated in gelatinous micro shell, may be sprinkled on a release liner 16, which is subsequently laminated to the skin barrier 12. The ostomy wafer 10 may be configured such that when the release liner 16 is removed prior to use, the skin friendly ingredients 18 transfer to the skin barrier 12 to provide the skin barrier 12 with the skin friendly ingredients 18 provided only on the skin contact surface 22 as shown in FIG. 3. When compared to skin barriers including skin friendly ingredients dispersed throughout the entire skin barrier matrix, the ostomy wafer 10 requires significantly less skin friendly ingredients, which may provide a substantial cost reduction. Further, since the skin friendly ingredients are provided only on the skin contact surface of a skin barrier, almost all of the skin friendly ingredients may come in contact with user's skin to maximize benefits provided by the skin friendly ingredients.

In some manufacturing processes, the skin friendly ingredients may be applied on a release liner or film prior to a skin barrier cookie being pressed onto the release liner or film to allow the skin friendly ingredients to transfer to the skin barrier. The skin friendly ingredients may be sprinkled on the release liner or film in powder form, or may be dissolved in a solvent or water and sprayed on the release liner or film. In some embodiments, the skin friendly ingredients may be applied directly on the skin contact surface of a skin barrier. Further, the skin friendly ingredients may be formulated to provide additional functions, such as improving skin barrier adhesion and/or other skin barrier properties, such as erosion.

The backing layer 14 may be formed from a suitable material, such as a gas-permeable, water-resistant material. Preferably, the backing layer 14 is highly flexible, so that it will conform readily to body contours and body movements, and relatively strong and durable.

Figure 4:
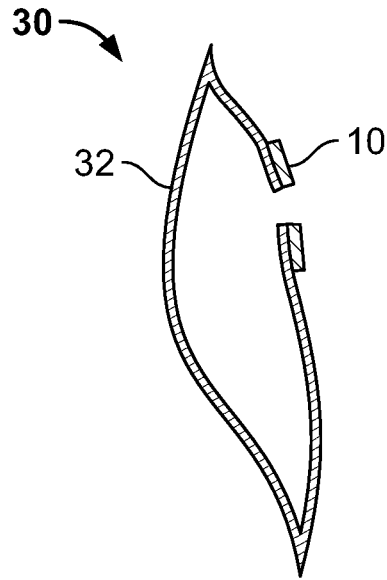
FIG. 4 is a schematic view of a one-piece ostomy pouch system including the ostomy wafer of FIG. 1 according to an embodiment.
Figure 5:
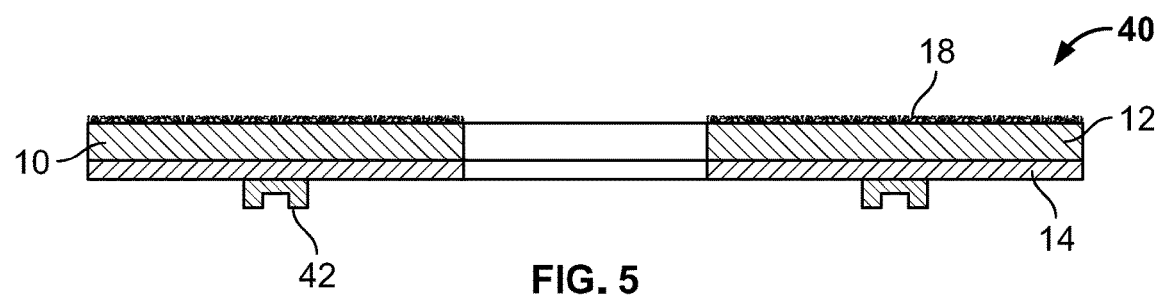
FIG. 5 is a cross-sectional view of a faceplate for a two-piece ostomy pouch system including a body-side coupling ring and the ostomy wafer of FIG. 1 according to an embodiment.
Figure 6:
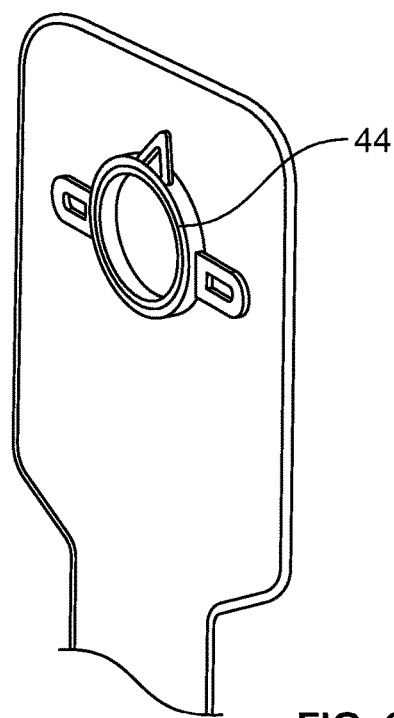
FIG. 6 is a perspective view of a pouch for a two-piece ostomy pouch system including a pouch-side coupling ring according to an embodiment.

The ostomy wafer 10 may be attached to a pouch 32 for a one-piece ostomy pouch 30 as shown in FIG. 4. Alternatively, the ostomy wafer 10 may be used to make a faceplate 40 including a body-side coupling ring 42 configured to engage a pouch-side coupling ring 44 for a two-piece ostomy pouch system as shown in FIGS. 5 and 6.

Figure 7:
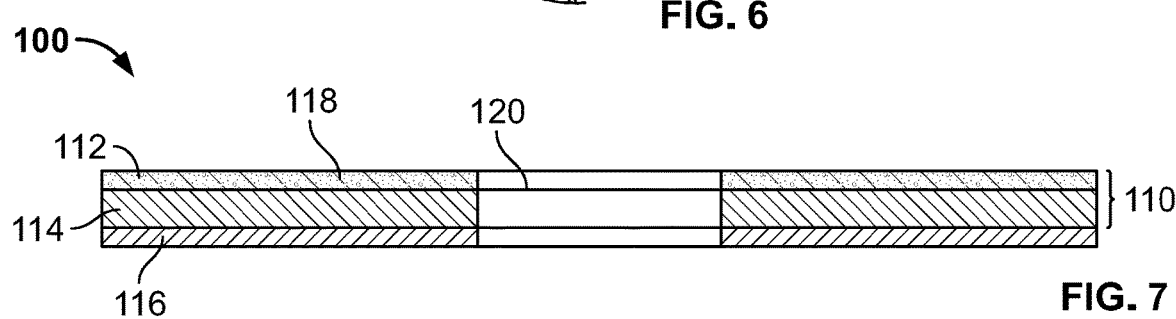
FIG. 7 is a cross-sectional view of an ostomy wafer according to another embodiment.

FIG. 7 is a cross-sectional illustration of an ostomy wafer 100 according to another embodiment. The ostomy wafer 100 may comprise a two-layer skin barrier 110, a backing layer 116, and an inlet opening 120 for receiving a stoma. The two-layer skin barrier 110 may include a first skin barrier layer 112 comprising skin friendly ingredients 118 and a second skin barrier layer 114. The skin friendly ingredients 118 may be dispersed in the first skin barrier layer 110. In an embodiment, the two-layer skin barrier 110 may be formed via a known coextrusion process, wherein the skin friendly ingredients are mixed with an adhesive formulation for the first skin barrier layer 110 and extruded. The first and second skin barrier layers 112, 114 may be formed from the same or different adhesive formulations.

In some embodiments, the first skin barrier layer 112 is thinner than the second skin barrier layer 112. For example, a thickness of the first skin barrier layer 112 may be less than about 50% of a thickness of the second barrier layer 114, preferably less than about 25%, more preferably less than about 15%.

Figure 8:
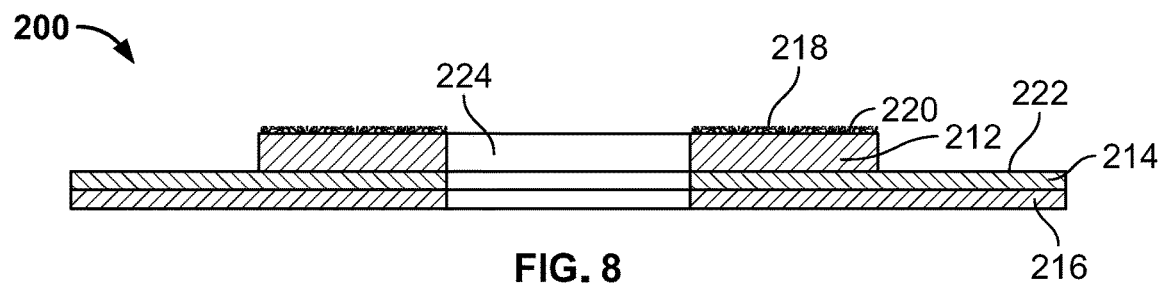
FIG. 8 is a cross-sectional view of an ostomy wafer according to yet another embodiment.

FIG. 8 is a cross-sectional illustration of an ostomy wafer 200 according to yet another embodiment. The wafer 200 may comprise a first adhesive 212, a second adhesive 214, a backing layer 216, and an inlet opening 224 for receiving a stoma. The first adhesive 212 may include skin friendly ingredients 218 provided only on a skin contact surface 220. The first adhesive 212 may be formed from a suitable pliable and tacky adhesive formulation capable of engaging and sealing the peristomal area, such as hydrophilic adhesives and skin barrier materials discussed in the foregoing embodiments. The second adhesive 214 may be formed from a hydrophilic adhesive or a hydrophobic adhesive, such as silicone adhesives or acrylic adhesives. The first and second adhesives 212, 214 may be formed from a same adhesive formulation or different adhesive formulations. In an embodiment, the first adhesive 212 may include a first skin contact layer and a second layer, wherein skin friendly ingredients are dispersed in the first skin contact layer. In some embodiments, skin friendly ingredients may also be provided on a skin contact surface 222 of the second adhesive 214.

Figure 9:
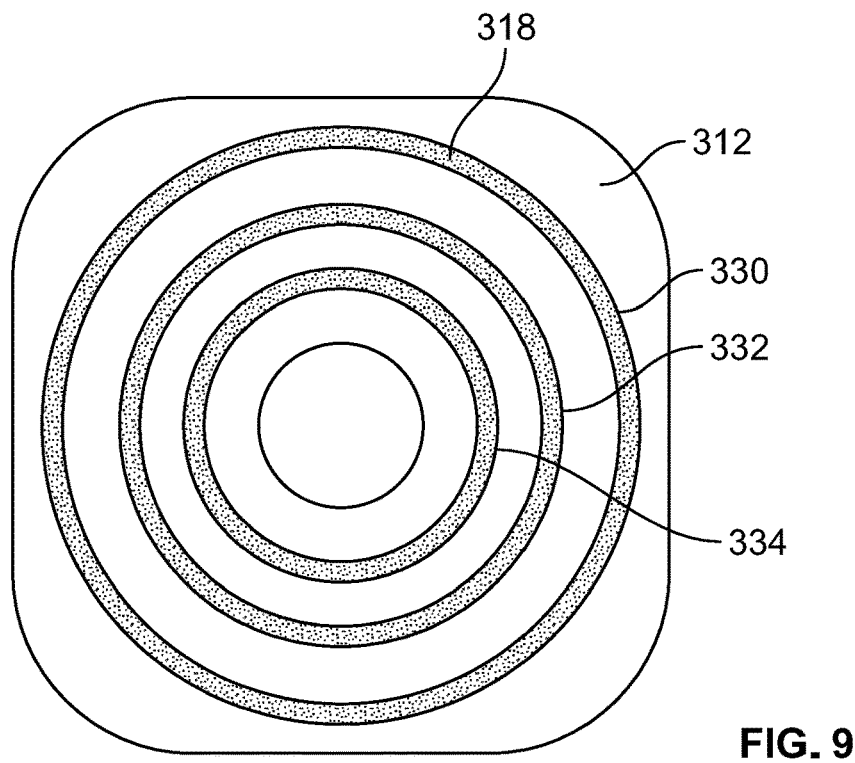
FIG. 9 is a schematic top view of an ostomy barrier including a pattern of skin friendly ingredients according to an embodiment.

In some embodiments, skin friendly ingredients may be provided on a portion of a skin contact surface. For example, skin friendly ingredients 318 may be provided in a pattern of concentric circles 330, 332, 334 on an ostomy skin barrier 312 as shown in FIG. 9. Although the pattern of the skin friendly ingredients 318 of FIG. 9 includes three concentric circles, the pattern of the skin friendly ingredients may include one or two circles, or more than three circles in other embodiments. The skin friendly ingredients may also be provided in various different patterns on a skin contact surface of a skin barrier.

In an embodiment, a layer of skin barrier material comprising skin friendly ingredients incorporated therein may be formed in a desired pattern and laminated to a skin contact surface of an ostomy skin barrier. For example, a layer of skin barrier material, which may be formed from the same or a different skin adhesive than that of the ostomy skin barrier 312, comprising skin friendly ingredients may be formed as concentric circles and laminated to the ostomy skin barrier 312 to form the pattern of concentric circles 330, 332, 334 as shown in FIG. 9. In another embodiment, the skin friendly ingredients may be injected into an ostomy skin barrier proximate a skin contact surface in desired shapes, patterns and depths, for example, using microneedles, to minimize any waste of skin friendly ingredients during manufacturing. For example, the skin friendly ingredients 318, such as microencapsulated skin friendly ingredients, may be injected into the ostomy skin barrier 312 to form the pattern of concentric circles 330, 332, 334. In an embodiment, a hydrophobic skin friendly adhesive may be provided to contour the outer periphery of the skin facing side of the ostomy skin barrier to minimize or prevent swelling and lifting of hydrocolloid adhesives and nonwoven fabric.

Figure 10:
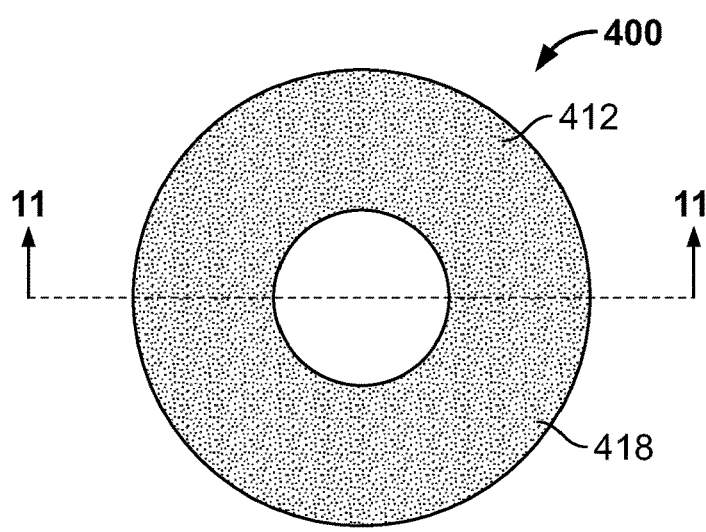
FIG. 10 is a schematic top view of a stoma ring according to an embodiment.
Figure 11:
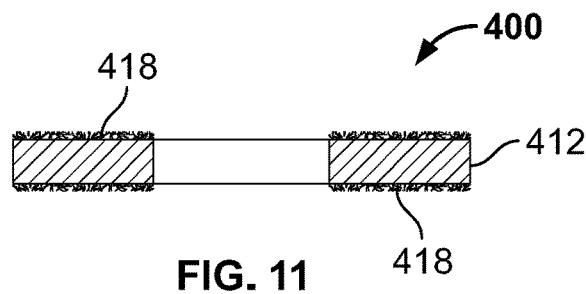
FIG. 11 is a cross-sectional view of the stoma ring of FIG. 10.

FIGS. 10 and 11 illustrate a stoma ring 400 according to an embodiment. The stoma ring 400 may generally comprise a stoma sealing material 412 and skin friendly ingredients 418 provides on outer surfaces of the stoma ring 400. The stoma sealing material 412 may be formed from a medical grade sealing material suitable for sealing around a stoma, such as hydrocolloid adhesives and silicone adhesives. The skin friendly ingredients 418 may be provided on at least a portion of the outer surfaces of the stoma ring 400 similar to the skin friendly ingredients 18, 118, 218, 318 of the foregoing embodiments. In an embodiment, the stoma ring 400 may comprise two outer layers and an inner layer arranged therebetween, wherein the outer layers comprise skin friendly ingredients incorporated therein.

Skin friendly ingredients may be provided on or incorporated into at least portion of an ostomy skin barrier or a stoma ring to maximize benefits to user's peristomal skin while maintaining sufficient tackiness and adhesive to support an ostomy pouch as it fills up with stoma effluent and to maintain leak-free seal around the stoma. In an embodiment, skin friendly ingredients may be provided such that the ostomy skin barrier or the stoma ring including the skin friendly ingredients may maintain at least about 85% of the original barrier properties of the ostomy skin barrier or the stoma ring without the skin friendly ingredients. Preferably, the ostomy skin barrier or the stoma ring including the skin friendly ingredients may have substantially the same barrier properties as the ostomy skin barrier or the stoma ring without the skin friendly ingredients. Further, the ostomy barrier or the stoma ring including the skin friendly ingredients may be configured such that the peelability or removability of the ostomy skin barrier or the stoma ring from a user after use is about the same as that of the ostomy barrier or the stoma ring.

A skin barrier comprising skin friendly ingredients only on a skin contact surface or in a skin contact layer may also be used for other skin-adhering devices, such as wound dressings and the like.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims

What is claimed is:

1. An ostomy wafer comprising a backing layer, a skin barrier, and an inlet opening for receiving a stoma, wherein the skin barrier is formed from a hydrocolloid adhesive and includes a skin contact layer and an inner layer, wherein at least one skin friendly ingredient is dispersed only in the skin contact layer, the skin contact layer is attached to user's peristomal skin, and the ostomy wafer is configured to support an ostomy pouch as it fills up with stoma effluent, and wherein the at least one skin friendly ingredient is selected from the group consisting of vitamin E, ceramide, cholesterol, fatty acids, micro-pockets of pH buffers, and anti-wrinkle agents, wherein a thickness of the skin contact layer is less than a thickness of the inner layer.

2. The ostomy wafer of claim 1, wherein the ostomy wafer is attached to the ostomy pouch for a one-piece ostomy pouch system.

3. The ostomy wafer of claim 1, wherein the ostomy wafer includes a body-side coupling ring configured to engage a pouch-side coupling ring attached to the ostomy pouch in a two-piece ostomy pouch system.

4. A stoma ring formed from a hydrocolloid adhesive and/or a silicone adhesive, wherein the stoma ring comprises a first outer surface layer, a second outer surface layer, and an inner layer arranged therebetween, and wherein at least one skin friendly ingredient is dispersed only in the first and second outer surface layers, wherein the at least one skin friendly ingredient is selected from the group consisting of vitamin E, ceramide, cholesterol, fatty acids, micro-pockets of pH buffers, and anti-wrinkle agents.

5. The ostomy wafer of claim 1, wherein the at least one skin friendly ingredient is provided in a pattern.

6. The ostomy wafer of claim 5, wherein the at least one skin friendly ingredient is provided in the pattern including at least two concentric circles.

* * * * *